United States Patent

Chang Lai

[11] Patent Number: 6,066,115
[45] Date of Patent: May 23, 2000

[54] SAFETY SYRINGE

[76] Inventor: Yu-Hau Chang Lai, No. 4, Da-Cheng Street, Taichung City, Taiwan

[21] Appl. No.: 09/361,111

[22] Filed: Jul. 27, 1999

[51] Int. Cl.⁷ .................................................. A61M 5/00
[52] U.S. Cl. .......................................... 604/110; 604/195
[58] Field of Search .................................. 604/192, 263, 604/110, 187, 195, 198

[56] References Cited

U.S. PATENT DOCUMENTS

| | | | |
|---|---|---|---|
| 5,273,543 | 12/1993 | Bell et al. | 604/110 |
| 5,336,186 | 8/1994 | Haber et al. | 604/110 |
| 5,634,903 | 6/1997 | Kurose et al. | 604/195 X |
| 5,688,240 | 11/1997 | Novacek et al. | 604/110 |
| 5,693,023 | 12/1997 | Adams | 604/195 |

FOREIGN PATENT DOCUMENTS

| | | |
|---|---|---|
| 165304 | 3/1997 | Taiwan . |
| 356720 | 4/1998 | Taiwan . |

*Primary Examiner*—John D. Yasko
*Attorney, Agent, or Firm*—Nixon & Vanderhye P.C.

[57] ABSTRACT

A safety syringe includes a barrel, a plunger, a needle set and a needle sheath. The plunger can be engaged with the needle set after completing an injection with the syringe, and the needle set can be then pulled in into the barrel for storage. Further, the needle set inside the barrel will pose automatically obliquely for avoiding the needle cannula being accidentally exposed exterior to the barrel.

6 Claims, 8 Drawing Sheets

SAFETY SYRINGE

BACKGROUND OF THE INVENTION

(1) Field of the Invention

The invention relates to a safety syringe, and more particularly to a syringe which is capable of retracting the needle cannula back into the barrel and then fixing the cannula in the barrel, after finishing an injection.

(2) Description of the Prior Art

Syringes are crucial parts for any medical treatment. To avoid accidental serum infection from a contagious disease, disposable syringes are usually used to prevent any syringe from being re-used. Nevertheless, inappropriate handling of the disposable syringes after usage was still seen, and the possibility of infection of a contagious disease for the medical staffs or the cleaners from accidental hurt by the disposed needle cannula always happened. Therefore, the measures of storing the disposed needle cannula and avoiding accidental infection caused from being hurt by the cannula are important topics nowadays while improving the syringe structure.

Generally, after an injection, the needle cannula is immediately retracted into and then stored in the barrel for further handling. For example, in Taiwanese Utility Model Publication No. 165304, an improved safety syringe structure is taught, in which a mating pair are assigned respectively to the extruding ring at end of the barrel and the pushing piston rod on top of the plunger; by providing the mating pair, the injection head having the needle cannula can be engaged with the pushing piston rod and then can be pulled in so as to be stored completely inside the barrel after an injection. In Taiwanese Utility Model Publication No. 356720, a safety syringe is disclosed, in which a threaded part at the bottom end of the needle cannula is introduced to be engaged with a small protruding block on top of the plunger for retracting the needle cannula into the barrel after usage.

SUMMARY OF THE INVENTION

Accordingly, it is an object of the present invention to provide a safety syringe, which can store the needle cannula inside the barrel after an injection, for preventing accidental infection caused from being stung by the needle cannula.

It is yet another object of the present invention to provide a safety syringe, in which the needle cannula can be effectively anchored inside the barrel for avoiding accidental exposure of the needle cannula and thus reducing the possibility of personal infection or hurt caused by needle sting.

It is a further object of the present invention to provide a safety syringe, which has advantages in simple structure, convenient application, and easy manufacturing.

To achieve all aforesaid objects, the safety syringe of the present invention comprises a barrel, a plunger, a needle set, and a needle sheath. The plunger has a rubber piston located at one end thereof, and the rubber piston includes a conical rod extruding from a surface thereof. The needle set includes an adapter having a conical hole thereon, and the conical hole is surrounded by a plurality of clipping means. After an injection, the conical rod of the rubber piston can be engaged with the conical hole of the needle set. Thereby, the needle set can be pulled completely into the barrel by the plunger. Further, the adapter of the needle set has a protrusion for slanting the needle set in the barrel, so that the needle cannula can be in contact with the inner wall of the barrel for avoiding accidental exposure exterior to the barrel.

BRIEF DESCRIPTION OF THE DRAWINGS

The present invention will now be specified with reference to its preferred embodiments illustrated in the drawings, in which.

DESCRIPTION OF THE PREFERRED EMBODIMENT

The invention disclosed herein is directed to a safety syringe. In the following description, numerous details are set forth in order to provide a thorough understanding of the present invention. It will be appreciated by one skilled in the art that variations of these specific details are possible while still achieving the results of the present invention. In other instances, well-known components are not described in detail in order not to unnecessarily obscure the present invention.

For simplifying the following descriptions, members with the same application will be designated by the same reference numerals.

Figure 1:
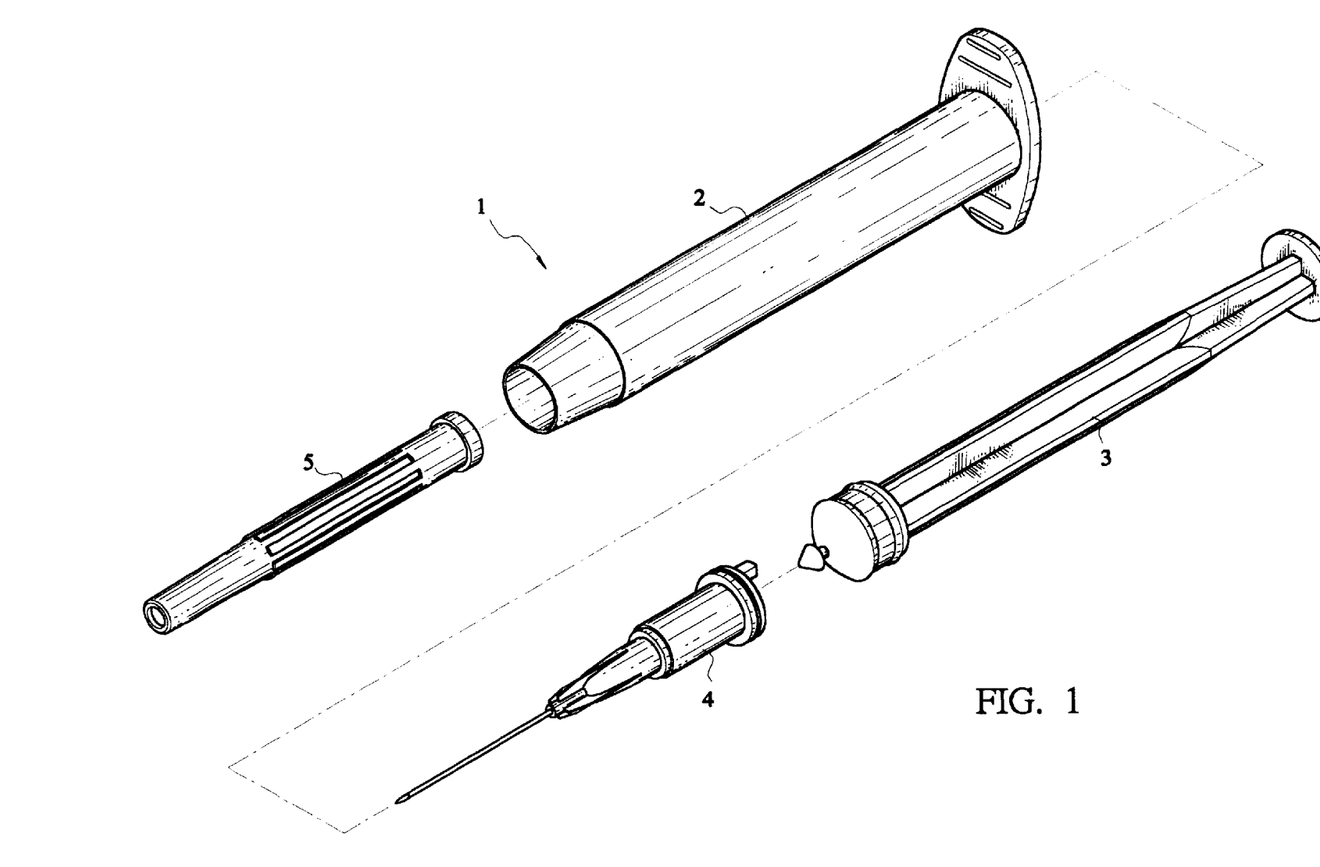
FIG. 1 is an exploded perspective view of an embodiment of the safety syringe in accordance with the present invention.

Referring now to FIG. 1, an first embodiment of the safety syringe 1 in accordance with the present invention is shown. The safety syringe 1 is a central type syringe with a needle cannula placed right in the center of front end of a barrel. The safety syringe 1 as shown includes a barrel 2, a plunger 3, a needle set 4 and a needle sheath 5.

Figure 2:
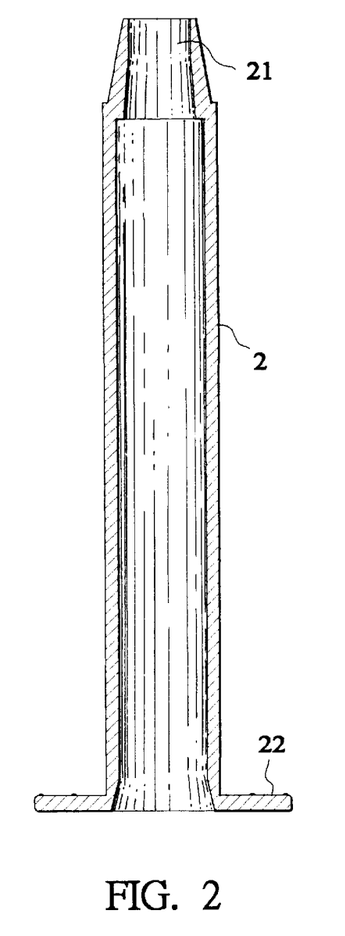
FIG. 2 is a cross-sectional view of the barrel in the embodiment of FIG. 1.

Referring to FIG. 2, the barrel 2 is a hollow cylindrical body with both ends open. A front end of the barrel 2 is structured as a nozzle 21 with a reduced inner diameter. A rear end of the barrel 2 is formed into a finger flange 22.

Figure 3:
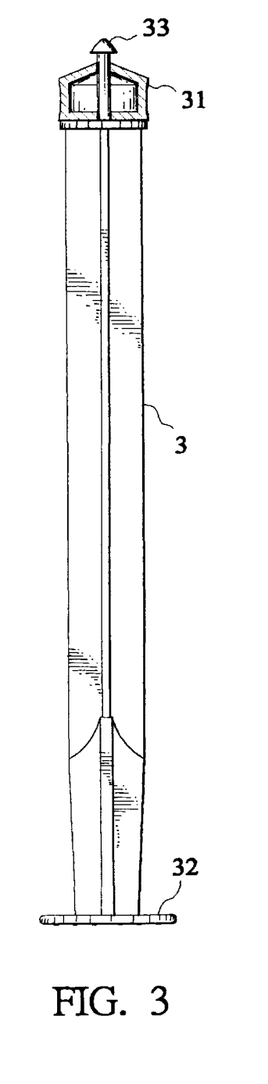
FIG. 3 is a partial cross-sectional view of the plunger in the embodiment of FIG. 1.

Referring to FIG. 3, the plunger 3 for being telescoped inside the barrel 2 has a front end carrying a rubber piston 31, in which the rubber piston 31 forms tight contact with the inner wall of the barrel 2 and is capable of sliding inside the barrel 2. A rear end of the plunger 3 is formed into a thumb rest 32. Further, the rubber piston 31 has a conical rod 33 located at a central part of a front surface thereof.

Figures 4A, 4B, 4C:
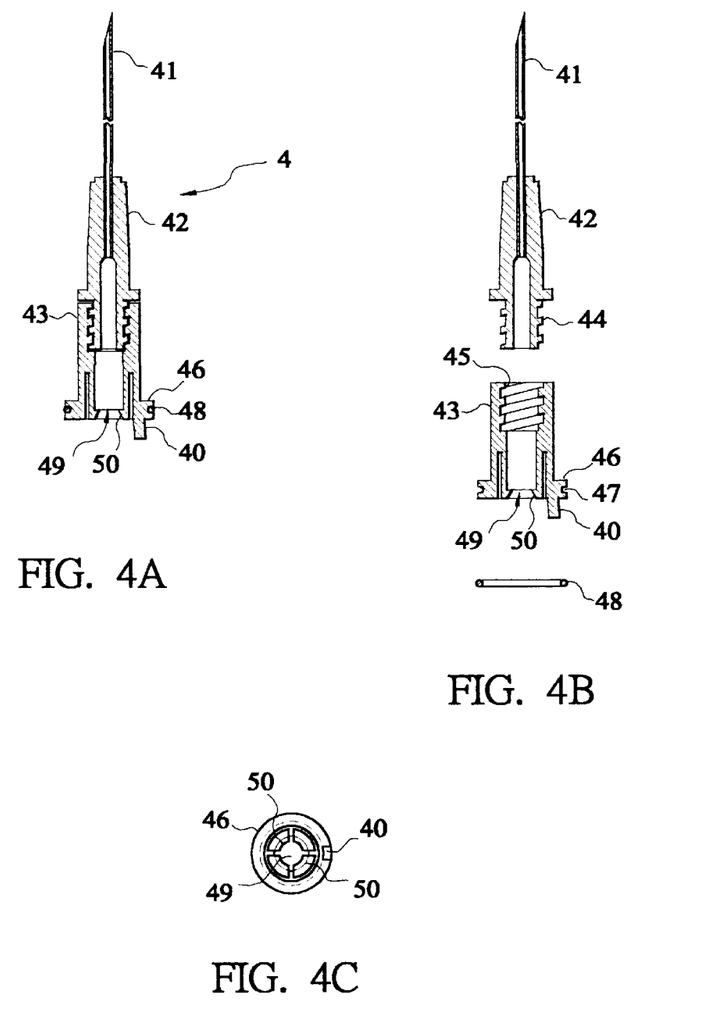
FIG. 4A is a cross-sectional view of the needle set in the embodiment of FIG. 1.
FIG. 4B is an exploded cross-sectional view of the needle set in the embodiment of FIG. 1.
FIG. 4C is a bottom view of the needle set in the embodiment of FIG. 1.

Referring to FIG. 4A to FIG. 4C, the needle set 4 consists of a needle cannula 41, a needle hub 42 for anchoring the needle cannula 41, and an adapter 43 for receiving the needle hub 42. The needle set 4 is telescopically placed inside the nozzle 21 of the barrel 2, with the needle cannula 41 being exposed to exterior of the barrel 2.

The needle hub 42 is provided with male threading 44 for meshing with female threading 45 on the adapter 43, as shown in FIG. 4A and FIG. 4B.

A rear part of the adapter 43 is formed with a base 46 with a protruding flange. The base 46 further includes a circumferential groove 47 for receiving a rubber seal 48 therein. By providing the rubber seal 48, a tight contact between the base 46 of the adapter 43 and the nozzle 21 of the barrel 2 can be established; as shown in FIG. 4A and FIG. 4B.

The base 46 of the adapter 43 is further formed with a conical hole 49 having a reducing diameter at a bottom thereof. As shown in FIG. 4C, the conical hole 49 is surrounded by a plurality of clipping means 50 symmetrically arranged in equal radial intervals. The plurality of clipping means 50 are formed with angular portions slanting inwards for defining the profile of the conical hole 49. Further, a protrusion 40 is formed at a proper location on the base 46 close to the conical hole 49.

The needle sheath 5 shown in FIG. 1 is located outside the nozzle 21 of the barrel 2 for shielding the needle cannula 41 of the needle set 4.

In the aforesaid embodiment of the safety syringe 1, the conical hole 49 is located at the center of the base 46 of the adapter 43, with the needle cannula 41 and the needle hub 42 being aligned with the fluid passage and the conical hole 49 of the adapter 43. Thus, a central injection-fluid route can be established in the needle set 4; as shown in FIG. 4A.

Figure 5A:
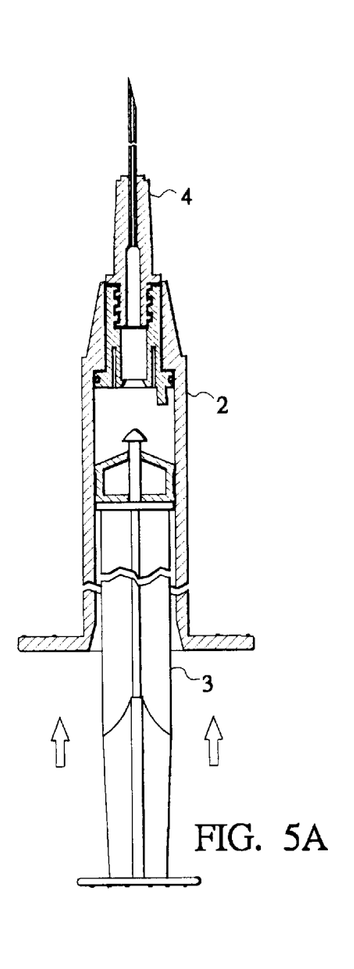
FIG. 5A is a cross-sectional view of the embodiment of FIG. 1, showing the plunger being pushed forward inside the barrel for an injection stroke.
Figure 5B:
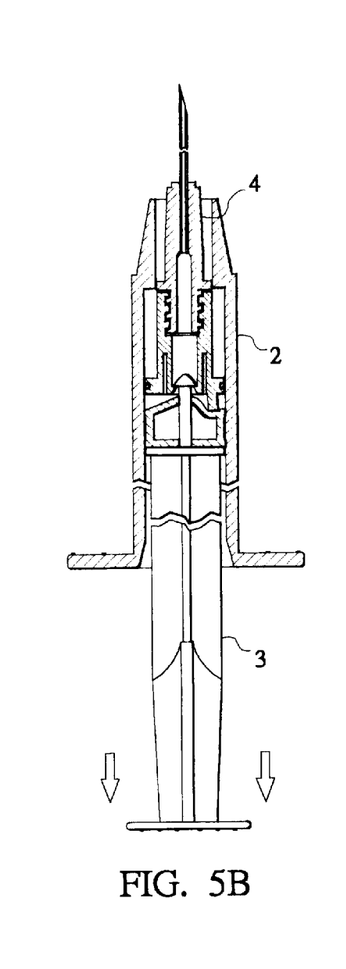
FIG. 5B is a cross-sectional view of the embodiment of FIG. 1, showing a pulling-back operation of the plunger after being engaged with the needle set.
Figure 5C:
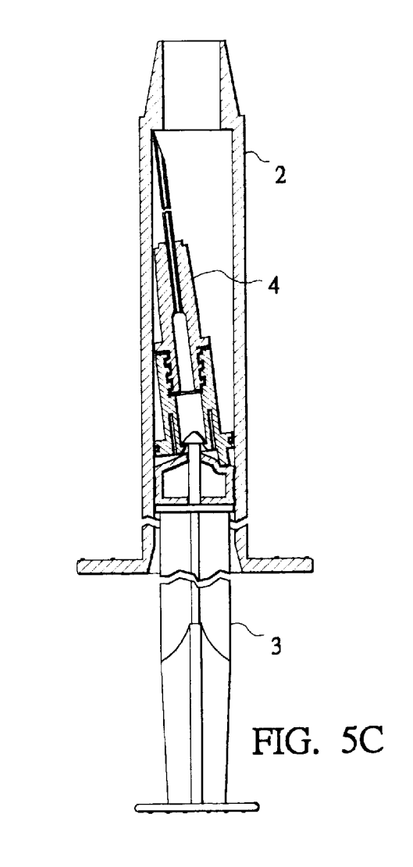
FIG. 5C is a cross-sectional view of the embodiment of FIG. 1, showing the needle set being completely received inside the barrel.
Figure 6:
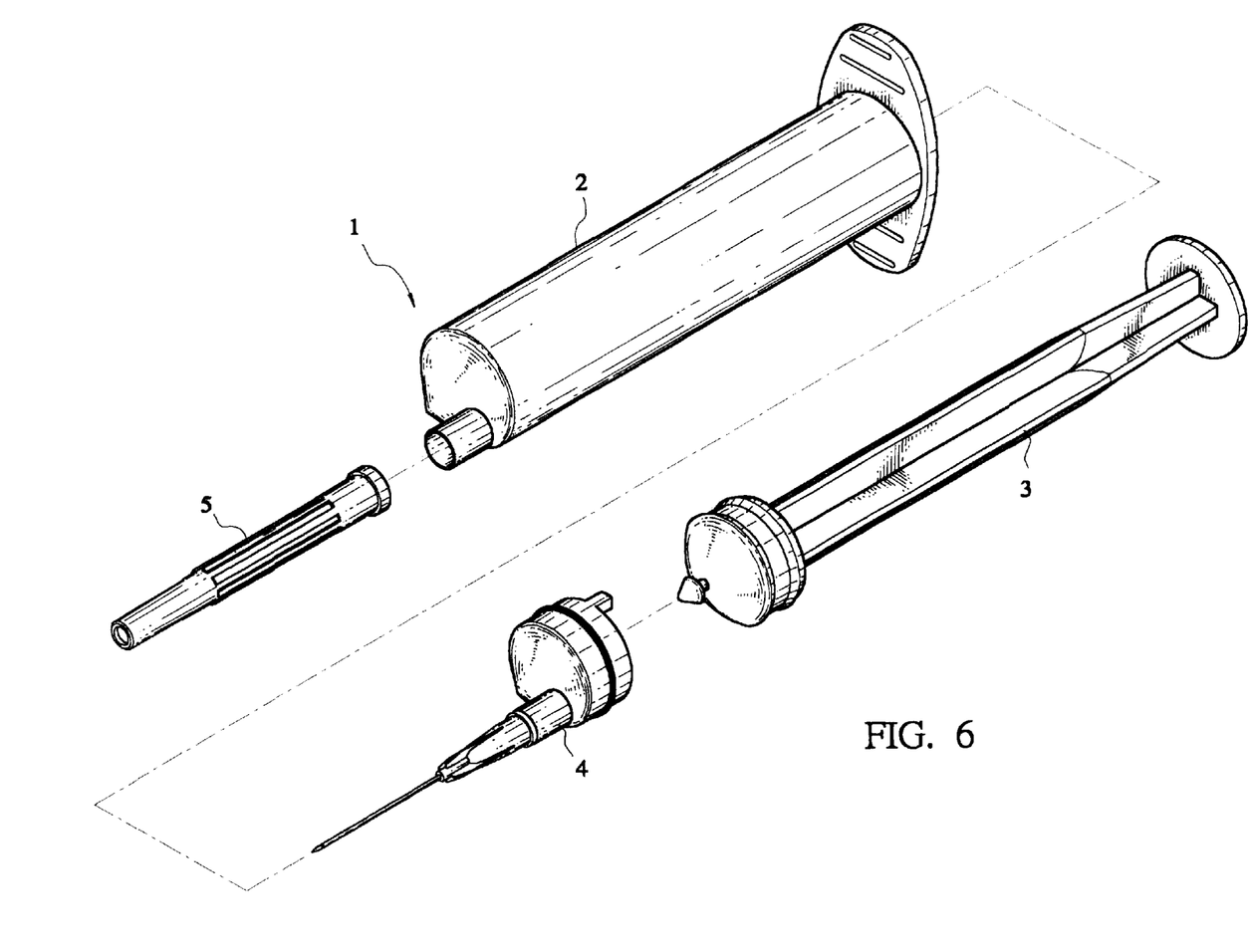
FIG. 6 is an exploded perspective view of another embodiment of the safety syringe in accordance with the present invention.
Figure 7:
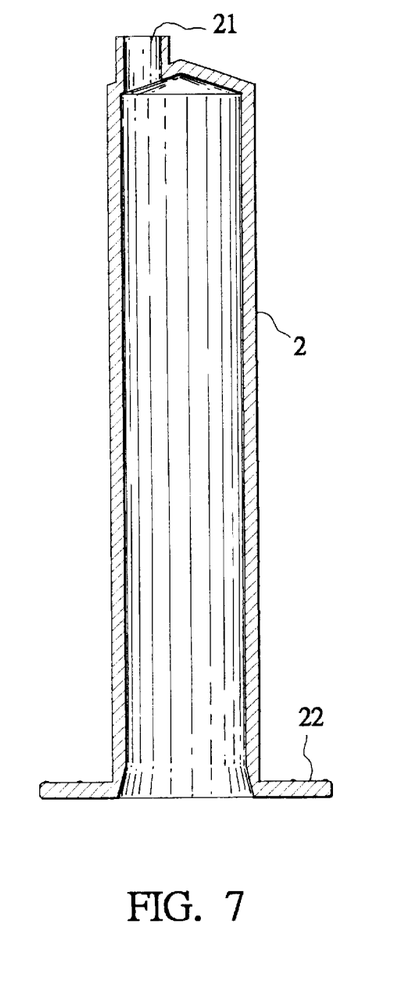
FIG. 7 is a cross-sectional view of the barrel in the embodiment of FIG. 6.
Figure 8:
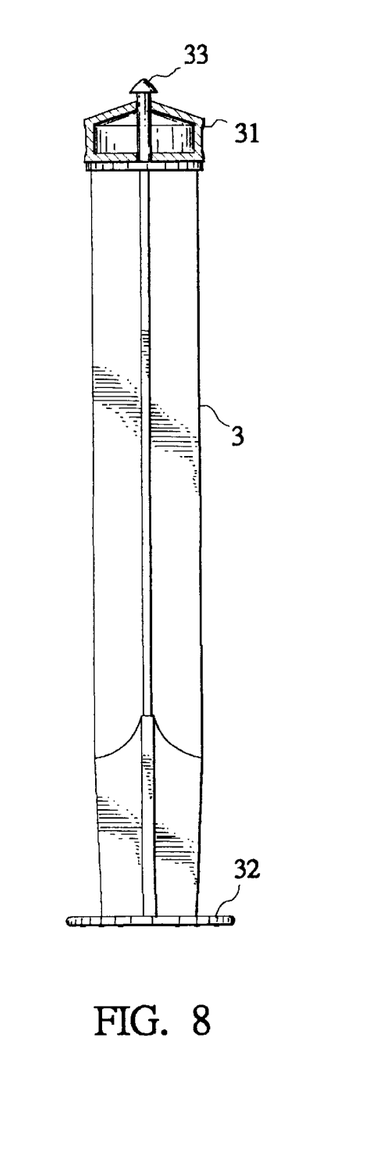
FIG. 8 is a partial cross-sectional view of the plunger in the embodiment of FIG. 6.

Referring to FIG. 5A through FIG. 5C, a complete application stroke of the safety syringe 1 in accordance with the present invention is shown. While beginning an injection stroke, the plunger 3 is firstly pushed forward (as shown in FIG. 5A). Then, at the moment that the plunger 3 reaches an extreme position, the conical rod 33 can be received into the conical hole 49 of the adapter 43. An engagement can be formed between the plunger 3 and the needle set 4 as the angular portions of the plurality of clipping means 50 inter-lock the conical rod 33, so that the conical rod 33 can be restrained from being taken off and will be firmly held inside the conical hole 49. After completing the engagement, the plunger 3 is retracted to pull in the needle set 4 into the barrel 2 through the nozzle 21 (as shown in FIG. 5B). While the needle set 4 is completely stored in the barrel 2, plastic force from the rubber piston 31 of the plunger 3 will push away the protrusion 40 of the adapter 43 to make the needle set 4 posed obliquely inside the barrel 2 (as shown in FIG. 5C). At this moment, by providing the needle set 4 to contact with the inner wall of the barrel 2, accidental exposure of the needle set 4 can then be substantially avoided.

Referring to FIG. 6 to FIG. 10C, a second embodiment of the safety syringe 1 in accordance with the present invention is shown. Apparently, the safety syringe 1 in this second embodiment is a lateral type of syringe with a needle cannula deviated from a centerline of a barrel.

Figure 9A:
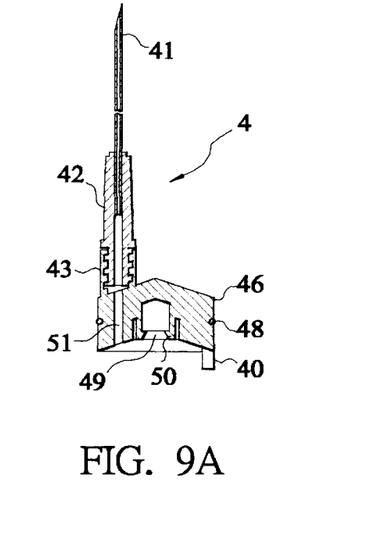
FIG. 9A is a cross-sectional view of the needle set in the embodiment of FIG. 6.
Figure 9B:
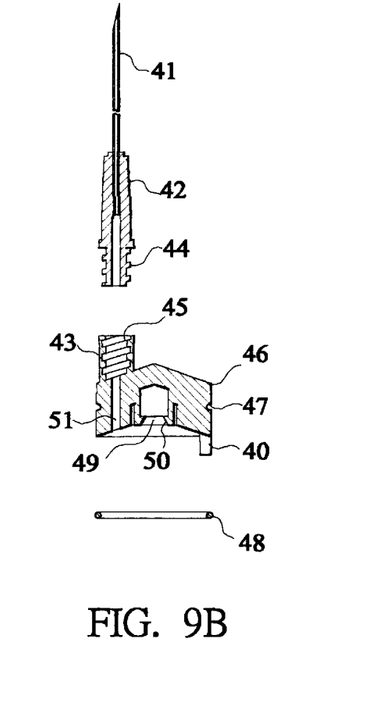
FIG. 9B is an exploded cross-sectional view of the needle set in the embodiment of FIG. 6.
Figure 9C:
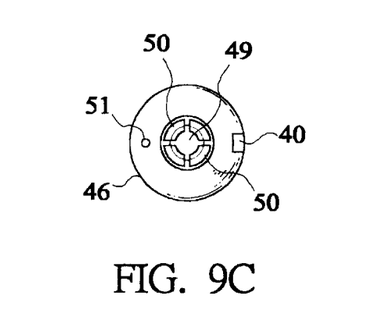
FIG. 9C is a bottom view of the needle set in the embodiment of FIG. 6.

In this embodiment, the conical hole 49 is still formed at the center of the base 46 of the adapter 43. Different only to the previous embodiment, the adapter 43 further includes a through-hole 51 aligned with the needle cannula 41 as well as the needle hub 42. The through-hole 51 located laterally to the conical hole 49 is used to form a lateral fluid route, as shown in FIG. 9A.

Figure 4D:
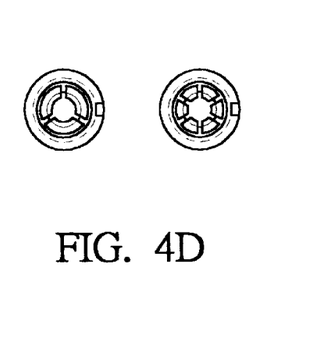
FIG. 4D is a bottom view showing other types of the bottom end of the needle set in the embodiment of FIG. 1.
Figure 9D:
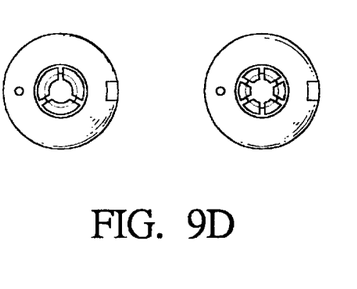
FIG. 9D is a bottom view showing other types of the bottom end of the needle set in the embodiment of FIG. 6.
Figures 10A, 10B:
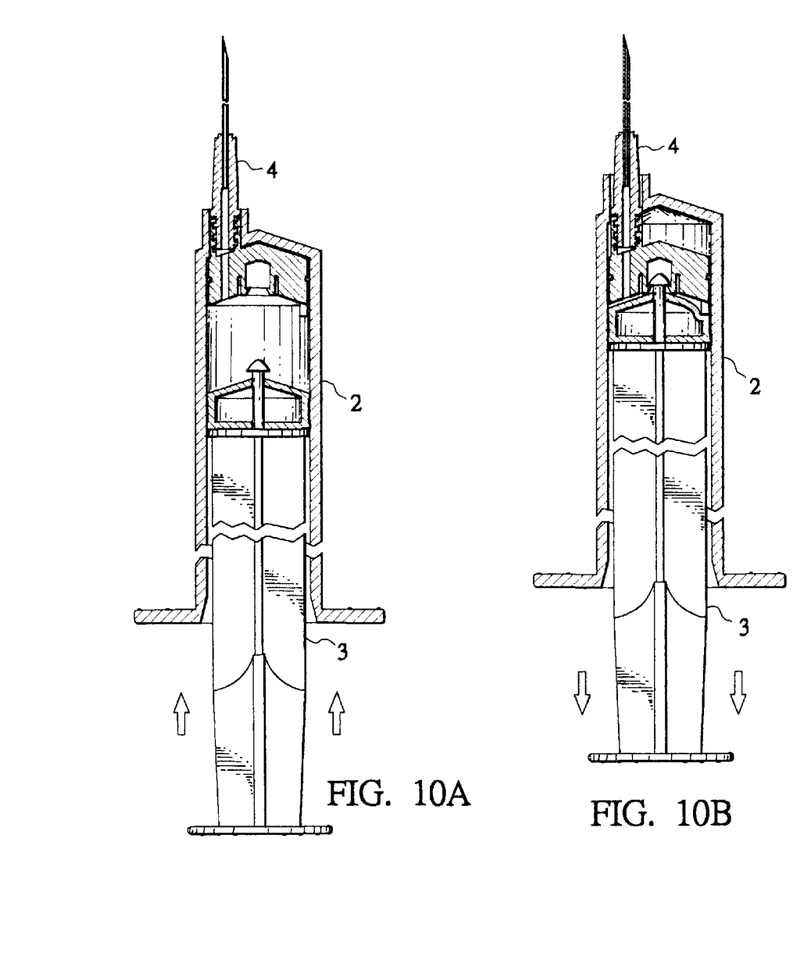
FIG. 10A is a cross-sectional view of the embodiment of FIG. 6, showing the plunger being pushed forward inside the barrel for an injection stroke.
FIG. 10B is a cross-sectional view of the embodiment of FIG. 6, showing a pulling-back operation of the plunger after being engaged with the needle set.
Figure 10C:
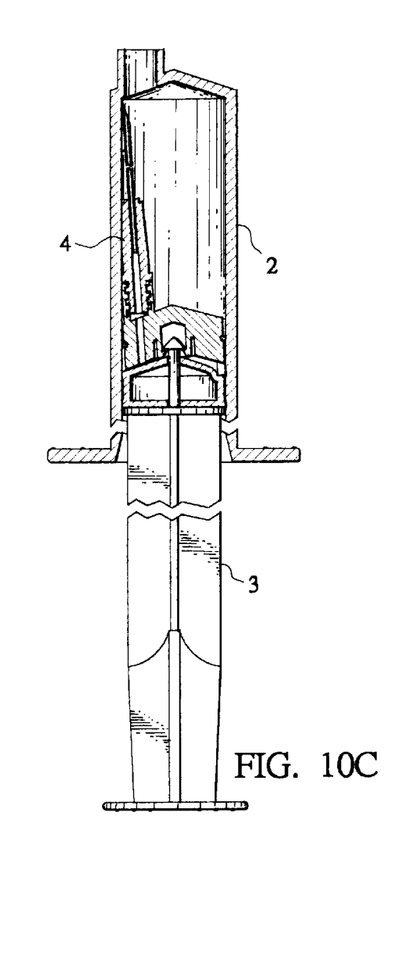
FIG. 10C is a cross-sectional view of the embodiment of FIG. 6, showing the needle set being completely received inside the barrel.

Further, in both the aforesaid embodiments, four symmetrically-spaced clipping means 50 (spaced by an angle of 90 degrees) are introduced. However, as required for other applications (such as using different materials or dimensions), other number of clipping means 50 can also be applied. For example, three clipping means 50 (spaced by an angle of 120 degrees) or six clipping means 50 (spaced by an angle of 60 degrees) can also be allowed in the present invention; as shown in FIG. 4D and FIG. 9D.

While the present invention has been particularly shown and described with reference to preferred embodiments, it will be understood by those skilled in the art that various changes in form and detail may be without departing from the spirit and scope of the present invention.

DESCRIPTION OF REFERENCE NUMERALS 1 (safety) syringe
2 barrel
3 plunger
4 needle set
5 needle sheath
21 nozzle
22 finger flange
31 rubber piston
32 thumb rest
33 conical rod
40 protrusion
41 needle hub
42 needle hub
43 adapter
44 male threading
45 female threading
46 base
47 groove
48 rubber seal
49 conical hole
50 clipping means
51 through hole

I claim:
1. A safety syringe, comprising:
a barrel, formed as a hollow cylindrical body having both ends thereof open, one end formed into a nozzle, another end formed into a finger flange;
a plunger, telescopically located inside the barrel, with one end thereof being provided with a rubber piston for forming tight contact with and sliding inside the barrel, and another end thereof being formed into a thumb rest;

a needle set, including a needle cannula, a needle hub for anchoring the needle cannula, and an adapter for receiving the needle hub, the needle set being telescopically placed inside the nozzle of the barrel with the needle cannula being exposed to exterior of the barrel; and a needle sheath, located outside the nozzle of the barrel for shielding the needle cannula of the needle set;

wherein the needle hub has male threading for meshing with female threading on the adapter;

the adapter has a base with a circumferential groove for receiving a rubber seal therein, the rubber seal forming a tight contact between the base and the nozzle;

the base of the adapter is formed with a conical hole having a reducing diameter at a bottom thereof, the conical hole being surrounded by a plurality of clipping means symmetrically arranged in equal radial intervals, the plurality of clipping means being formed with angular portions slanting inwards for defining the profile of the conical hole, and a protrusion being formed at a proper location on the base close to the conical hole; and the rubber piston of the plunger is provided with a conical rod for being received into the conical hole of the adapter to form a mutual engagement.

2. The safety syringe according to claim 1, wherein said conical hole is located at the center of the base of the adapter so as to be aligned with the needle cannula and the needle hub.

3. The safety syringe according to claim 1, wherein said conical hole is located at the center of the base of the adapter, and the needle cannula as well as the needle hub are aligned with a through-hole of the adapter for forming a lateral fluid route with the conical hole.

4. The safety syringe according to claim 1, wherein said conical hole is surrounded by three said symmetrically-arranged clipping means.

5. The safety syringe according to claim 1, wherein said conical hole is surrounded by four said symmetrically-arranged clipping means.

6. The safety syringe according to claim 1, wherein said conical hole is surrounded by six said symmetrically-arranged clipping means.

* * * * *